US008673886B2

(12) United States Patent (10) Patent No.: US 8,673,886 B2
Mailland (45) Date of Patent: Mar. 18, 2014

(54) **USE OF NIFURATEL TO TREAT INFECTIONS CAUSED BY *ATOPOBIUM* SPECIES**

(75) Inventor: Federico Mailland, Lugano (CH)

(73) Assignee: Polichem SA, Luxembourg (LU)

( * ) Notice: Subject to any disclaimer, the term of this patent is extended or adjusted under 35 U.S.C. 154(b) by 24 days.

(21) Appl. No.: 13/138,896

(22) PCT Filed: Apr. 19, 2010

(86) PCT No.: PCT/EP2010/055090
§ 371 (c)(1),
(2), (4) Date: Oct. 19, 2011

(87) PCT Pub. No.: WO2010/121980
PCT Pub. Date: Oct. 28, 2010

(65) Prior Publication Data
US 2012/0035124 A1 Feb. 9, 2012

(30) Foreign Application Priority Data
Apr. 20, 2009 (EP) .................................. 09158221

(51) Int. Cl.
*A61K 31/655* (2006.01)
(52) U.S. Cl.
USPC ....................................................... 514/158
(58) Field of Classification Search
USPC ....................................................... 514/158
See application file for complete search history.

(56) References Cited

U.S. PATENT DOCUMENTS

| 6,416,779 | B1 * | 7/2002 | D'Augustine et al. | ........ 424/430 |
| 7,619,008 | B2 * | 11/2009 | Yang et al. | .................... 514/738 |
| 2007/0059298 | A1 * | 3/2007 | Volkmann | .................. 424/93.45 |
| 2008/0268006 | A1 * | 10/2008 | Molin et al. | .................. 424/402 |

FOREIGN PATENT DOCUMENTS

| CN | 101019864 | 8/2007 |
| CN | 101199474 | 6/2008 |

OTHER PUBLICATIONS

Bradshaw, C S, et al., Journal of Infectious Diseases, vol. 194, No. 6, p. 826-836, Sep. 15, 2006.
Ellen De Backer, et al., BMC Infectious Diseases, vol. 6, No. 1, p. 51 Abstract, Mar. 16, 2006.
International Preliminary Report on Patentability for PCT/EP2010/055090 of Jan. 25, 2011.
International Search Report for PCT/EP2010/055090 of Jun. 1, 2010.
Jovita Rodriguez, et al., International Journal of Systematic Bacteriology, vol. 49, No. Part 4, p. 1573-1576, Oct. 1, 1999.
Mendling Werner, et al., Arzneimittel Forschung. vol. 52, No. 1, p. 8-13, Jan. 1, 2002.
FDA Guideline Summary NGC-6014, "National guideline for the management of bacterial vaginosis", 2006.
Collins, et al. Comparative sequence analyses of the 16s rRNA genes of *Lactobacillus minutus, Lactobacillus rimae* and *Streptococcus parvulus*: Proposal for the creation of a new genus *Atopobium*, FEMS Microbiology Letters, 95: 235-240, 1992.
Ferris, et al., Association of *Atopobium vaginae*, a recently described metronidazole resistant anaerobe, with bacterial vaginosis, BMC Infectious Diseases, vol. 4(5), pp. 1-8, Feb. 13, 2004.
Rodriguez Jovita, et al., Characterization of a novel *Atopobium* isolate from the human vagina:description of *Atopobium vaginae* sp. nov., International Journal of Systematic Bacteriology, 49:1573-1576, 1999.
Togni, et al., In Vitro activity of nifuratel on vaginal bacteria: Could it be a good candidate for the treatment of bacterial vaginosis?, Antimicrobial Agents and Chemotherapy, vol. 55, No. 5, p. 2490-2492. May 2011.
Wikipedia, Sep. 24, 2013. Gardnerella vaginalis, http://en.wikipedia.org/wiki/Gardnerella[13] vaginalis.

* cited by examiner

*Primary Examiner* — Elli Peselev
(74) *Attorney, Agent, or Firm* — Hueschen and Sage

(57) ABSTRACT

The present invention is directed to the use of nifuratel, or a physiologically acceptable salt thereof, to treat infections caused by *Atopobium* species. The invention is further directed to the use of nifuratel to treat bacteriuria, urinary tract infections, infections of external genitalia in both sexes, as well as bacterial vaginosis, or mixed vaginal infections in women, when one or more species of the genus *Atopobium* are among the causative pathogens of those infections.

25 Claims, No Drawings

USE OF NIFURATEL TO TREAT INFECTIONS CAUSED BY *ATOPOBIUM* SPECIES

The present invention relates to the use of nifuratel, or a physiologically acceptable salt thereof, to treat infections caused by *Atopobium* species. The invention is further directed to the use of nifuratel to treat bacteriuria, urinary tract infections, infections of external genitalia in both sexes, as well as bacterial vaginosis, or mixed vaginal infections in women caused by one or more species of the genus *Atopobium*.

BACKGROUND OF THE INVENTION

Bacterial vaginosis is considered as a common vaginal disorder in women of reproductive age. Whereas the normal vaginal flora consists of lactobacilli, especially *L. crispatus*, the disturbed vaginal microflora was mainly characterized in the past by the overgrowth of *Gardnerella vaginalis* (formerly known as *Haemophilus vaginalis*) and anaerobic bacteria such as *Mobiluncus* spp., *Mycoplasma hominis* and *Prevotella* spp. More recently, the interest for bacterial vaginosis increased because of reports of adverse sequelae of this disorder, such as preterm birth (Hay P E et al. Brit Med J 1994, 308:295-298), pelvic inflammatory disease (Haggerty C L et al. Clin Infect Dis 2004, 39:990-995) and postpartum endometritis (Watts D H et al. Obstet Gynecol 1990, 75:52-58).

The severity of the consequences of those sequelae asks for an adequate treatment of bacterial vaginosis. In the art, the drug of choice in the treatment of bacterial vaginosis is oral or topical metronidazole, a nitroimidazole derivative, which is considered as the golden standard in the management of non mycotic vaginal infections. Metronidazole is an antiprotozoarian drug, endowed with therapeutic effect in genital protozoarian infections of both sexes, like trichomoniasis, and also on protozoarian infections of gastrointestinal tract, like intestinal amoebiasis due to *Giardia lamblia*. Metronidazole is also provided of an inhibitory effect on the growth of *Gardnerella vaginalis* and other bacteria, but is not considered as an antibiotic as it has no effect on the normal flora of lactobacilli. Nifuratel is a nitrofurane derivative and is considered as the alternative to metronidazole, being endowed of similar effect on protozoa (*Trichomonas* and *Giardia lamblia*) and on *Gardnerella*, with no effect on lactobacilli. Thus, metronidazole and nifuratel are both antiprotozoarian drugs, with an inhibitory effect on *Gardnerella*.

Recently, it has been put in evidence that a new microorganism, named *Atopobium vaginae*, is strongly associated with bacterial vaginosis (Verstraelen H et al. Am J Obstet Gynecol 2004, 191:1130-1132) and is likely the cause of failure to metronidazole treatment and of relapses. *Atopobium* is an anaerobe bacteria never described before, a metronidazole resistant organism, that may account for the antimicrobial resistance (up to 30%) associated with the treatment of bacterial vaginosis with metronidazole (Larsson P G et al. APMIS 2005, 113:305-316). *Atopobium vaginae* has been described to constitute a consistent part of the bacteria that form an adherent biofilm on the vaginal epithelium even after standard therapy with metronidazole (Swidsinski A, Mendling W et al. Am J Obstet Gynecol 2008; 198:97.e1-97.e6) and has been found in urine and in urinary epithelium of male partners of women with bacterial vaginosis.

It has now surprisingly been found that nifuratel, a drug with an antimicrobial spectrum similar to that of metronidazole, is provided of an inhibitory effect on the growth of strains of *Atopobium*, that are resistant to metronidazole.

DESCRIPTION OF THE INVENTION

The object of the present invention is represented by the use of nifuratel, or a physiologically acceptable salt thereof, for use in the treatment of any infection caused by *Atopobium* species. More particularly, it is represented by the use of nifuratel, or a physiologically acceptable salt thereof, for treating bacteriuria, urinary tract infections, infections of external genitalia in both sexes, as well as bacterial vaginosis, or mixed vaginal infections in women, when one or more species of the genus *Atopobium* are among the causative pathogens of those infections.

Solid, semi-solid or liquid preparations of nifuratel or of a physiologically acceptable salt thereof, in the form of oral tablets, capsules, dragées or syrup, or topical cream, ointment, gel, lotion, foam, to be applied deeply into the vagina or over the external genitalia, the vulva, the perivulvar area, or the penis, or vaginal tablets, capsules or pessaries, to put deeply into the vagina, with a content in nifuratel from 1 to 1000 mg per single dose, more preferably from 10 to 500 mg per single dose, most preferably from 50 to 400 mg per single dose, are suitable to treat infections by *Atopobium*; such preparations may be administered in infected patients according to conventional techniques; according to a preferred embodiment, they are administered on a regular basis, preferably daily.

Pharmaceutical compositions may be prepared according to conventional techniques, may contain pharmaceutically acceptable excipients, adjuvants and/or carriers, and may also contain, in combination, one or more active principles with complementary or, in any case, useful activity. The active agents which may be used in combination with nifuratel of the present invention include, but are not limited to, antibiotics, antifungal agents, antiseptic agents, pH modifiers, probiotics; such active ingredients may be administered together with nifuratel (i.e. they may be for instance contained in the same composition as nifuratel) or they may be administered separately from or in temporal proximity with nifuratel.

Examples of antibiotics include clindamycin, macrolide antibiotics such as erythromycin, oleandomycin, flurithromycin, azithromycin and claritromycin and salts thereof, beta-lactam antibiotics such as penicillin, ampicillin, amoxicillin and salts thereof, fluoroquinolones such as ofloxacine, norfloxacine, ciprofloxacine and salts thereof, aminoglycosides such as gentamycin, amikacin, kanamycin, neomycin and salts thereof.

Examples of antifungal agents include: 1-hydroxy-2-pyridone compounds and their salts, e.g. ciclopirox, rilopirox, piroctone, ciclopirox olamine; imidazole derivatives and their salts, e.g. clotrimazole, econazole, isoconazole, ketoconazole, miconazole, tioconazole, bifonazole, fenticonazole and oxiconazole; polyene derivatives and their salts, e.g. nystatin, natamycin and amphotericin; allylamine derivatives and their salts, e.g. naphtifine and terbinafine; triazole derivatives and their salts, e.g. fluconazole, itraconazole, terconazole and voriconazole; morpholine derivatives and their salts, e.g. amorolfine and morpholines disclosed in U.S. Pat. No. 5,120, 530, herein incorporated by reference; griseofulvin and related compounds, e.g. griseofulvin; undecylenic acid and its salts, in particular, the zinc and calcium salts of undecylenic acid; tolnaphtate and its salts; and flucytosine and its salts.

The antimycotic agent may also be selected from natural sources, in particular plant extracts. Examples of these extracts include tea tree oil (*Melaleuca alternifolia*), lavender oil (*Lavandula officinalis* chaix) and the leaf extract of the neem tree (*Azadirachta indica*).

Examples of the antiseptic agents include: benzalkonium-chlorid, benzethonium-chlorid, cetrimonium-bromid, chlorhexidin, dequaliniumchlorid, triclocarban, triclosan, salicylic acid, benzoic acid and their salts, p-hydroxybenzoic acid and its esters.

Examples of pH modifiers include: ascorbic acid, acetic acid, lactic acid, and salts thereof.

Examples of probiotics include species of the genus *Lactobacillus*.

Examples of the compositions prepared according to the present invention include: tablets, capsules, dragées or syrup suitable for oral administration; topical cream, ointment, gel, lotion, foam, to be applied deeply into the vagina or over the external genitalia, the vulva, the perivulvar area, or the penis, the glans, or the balano-preputial skinfold; vaginal tablets, capsules or pessaries, to put deeply into the vagina.

The pharmaceutical compositions and the uses of the present invention will now be more fully described by the following examples. It should, however, be noted that such examples are given by way of illustration and not of limitation.

EXAMPLE 1

Oral tablet are produced with the following quali-quantitative formula:

| Ingredients | Quantity (mg/tablet) |
| --- | --- |
| 1. Nifuratel | 200.00 |
| 2. Maize starch | 65.00 |
| 3. Talc | 30.00 |
| 4. Polyethylene glycol 6000 | 14.00 |
| 5. Magnesium stearate | 2.00 |

The process consists on the preparation (protecting from light) of binder solution with water and polyethylene glycol heat at 45° C. under continuous stirring; then granulate in a Glatt fluid bed basket by blending nifuratel and starch until the mass is homogeneous, before spraying with the binder solution, then dry at inlet air temperature of 60° C.; then add talc and magnesium stearate. Tabletting is done in a rotary tabletting machine with an appropriate punch.

The obtained tablet has a smooth surface with a yellow colour.

EXAMPLE 2

An in vitro study was performed to investigate the susceptibility of *Atopobium vaginae* to nifuratel, compared to metronidazole. Ten strains of *Atopobium vaginae* (Culture Collection Centre, University of Göteborg, Sweden) were incubated in Columbia blood agar plates (5% (v/v) sheep blood) for 3 days at 36±1° C. under anaerobic conditions. *Brucella* agar supplemented with 5 g hemin, 1 µg vitamin K1 per ml and 5% (v/v) sheep blood was used for minimum inhibiting concentration (MIC) determination.

Nifuratel and metronidazole (previously dissolved in dimethyl sulfoxide) were added to the medium. The ranges of the concentrations tested were 0.125-256 µg/ml for both nifuratel and metronidazole.

The results were as follows: nifuratel inhibited the growth of all strains, with MICs between 0.15 and 1 µg/ml, while metronidazole was effective on that pathogen just at high/very high concentrations (8-256 µg/ml), as reported in Table 1. As the value of MIC is commonly considered as the measure of susceptibility of a microbiota to an antimicrobial agent, it is concluded that *Atopobium* was sensitive to Nifuratel while it was resistant to metronidazole.

TABLE 1

Comparison of MICs for different strains of *Atopobium vaginae*

| Strain | Nifuratel µg/mL | Metronidazole µg/mL |
| --- | --- | --- |
| CCUG 38953T | 1 | 156 |
| CCUG 42099 | 0.5 | 264 |
| CCUG 43049 | 0.25 | 16 |
| CCUG 44061 | 1 | 64 |
| CCUG 44116 | 0.5 | 32 |
| CCUG 44125 | 0.25 | 16 |
| CCUG 44156 | 0.125 | 8 |
| CCUG 44258 | 0.5 | 32 |
| CCUG 48515 | 0.5 | 32 |

EXAMPLE 3

A syrup having the following composition wt./wt. % is prepared:

| Ingredients | Quantity (g/100 ml syrup) |
| --- | --- |
| 1. Nifuratel | 4.0 |
| 2. Polysorbate 80 | 0.04 |
| 3. Sorbitol 70% | 20.0 |
| 4. Glycerol | 10.0 |
| 5. Sucrose | 30.0 |
| 6. Citric acid, monohydrate | 0.1 |
| 7. Methyl-parahydroxybenzoate | 0.07 |
| 8. Propyl-parahydroxybenzoate | 0.03 |
| 9. Sodium chloride | 0.04 |
| 10. Carboxymethyl cellulose | 0.6 |
| 11. silicon dioxide | 2.0 |
| 12. Deionised water q.s. | ml 100 |

Preparation

The formulation is prepared (protecting from light) as follows:

1) a gel is prepared with deionised water and carboxymethyl cellulose (3.75% in water). The gel is left to swallow overnight.
2) a solution of water, sucrose (50%) and sodium chloride (0.5%) is prepared apart.
3) a mixture of nifuratel (0.4%) and Polysorbate 80 (1%) is prepared in water. The mixture is stirred until it becomes homogeneous.
4) In a closed vessel with a stirrer are added deionised water, sorbitol and glycerol, the solution 2) and sucrose. The mixture is maintained under continuous stirring. Then add methyl-parahydroxybenzoate, propyl-parahydroxybenzoate and silicon dioxide. Heat at 100° C. under stirring for 30 minutes. Cooling at 80° C. citric acid is added. Then cooling at 40° C., add the gel 1) and the preparation 3) under continuous stirring.

The resulting syrup is a homogeneous suspension.

EXAMPLE 4

A vaginal tablet having the following composition is prepared:

| Ingredients | Quantity (mg/tablet) |
| --- | --- |
| 1. Nifuratel | 250 |
| 2. Maize starch | 500 |
| 3. Lactose | 500 |
| 4. Polyethylen glycol 6000 | 120 |
| 5. Tartaric acid | 25 |
| 6. Sodium bicarbonate | 25 |
| 7. Magnesium stearate | 30 |

Preparation

The formulation is prepared (protecting from light) as described below.

A mixture of nifuratel, lactose and maize starch is put into the fluid bed granulator/dryer and granulated with a binder solution prepared with maize starch, polyethylen glycol 6000 and water. After a suitable period of drying, the granulate is mixed with magnesium stearate, tartaric acid and sodium bicarbonate and then transferred to a tabletting machine: a yellow tablet with a smooth surface is obtained.

EXAMPLE 5

A cream formulation having the following composition is prepared:

| Ingredients | Quantity (g/100 g cream) |
| --- | --- |
| 1. Nifuratel | 10.0 |
| 2. Nystatine | I.U. 4,000,000 |
| 3. Xalifin 15* | 10.0 |
| 4. Methyl-parahydroxybenzoate | 0.11 |
| 5. Propyl-parahydroxybenzoate | 0.04 |
| 6. Glycerol | 5.0 |
| 7. Sorbitol 70% | 10.0 |
| 8. Propylene glycol | 5.0 |
| 9. Carbomer | 0.4 |
| 10. Triethanolamine 30% w/v | 1.5 |
| 11. Purified water q.s. | g 100 |

*Polyglycolic esters of fatty acids

Preparation

In a closed vessel with a stirrer are added water, carbomer, glycerol and propylene glycol. To the resulting solution are added nifuratel, nystatine, the two preservatives, the Xalifin 15 and the other ingredients.

The emulsion obtained is a homogeneous cream of yellow colour.

The invention claimed is:

1. A method of treating an infection in a subject caused by *Atopobium vaginae* comprising the step of administering nifuratel, or a physiologically acceptable salt thereof, to the subject in an amount effective to inhibit the growth of the *Atopobium vaginae*.

2. The method of claim 1, wherein the infection is selected from bacteriuria, urethritis, urinary infections and infections of external genitalia in men and/or women.

3. The method of claim 1, wherein the infection is selected from bacterial vaginosis and mixed vaginal infections in women.

4. The method of claim 1, wherein the nifuratel, or a physiologically acceptable salt thereof, is administered to the subject in the form of a pharmaceutical formulation selected from tablets; capsules; dragées; syrup for oral administration; topical cream; ointment; gel; lotion; a foam applied deeply into the vagina or over the external genitalia, the vulva, the perivulvar area, the penis, the glans, or the balano-preputial skinfold; vaginal tablets; vaginal capsules; and vaginal pessaries.

5. The method of claim 4, wherein the pharmaceutical formulation comprises nifuratel, or a physiologically acceptable salt thereof, in an amount from 1 to 1000 mg per single dose.

6. The method of claim 4, wherein the pharmaceutical formulation comprises nifuratel, or a physiologically acceptable salt thereof, in an amount from 10 to 500 mg per single dose.

7. The method of claim 4, wherein the pharmaceutical formulation comprises nifuratel, or a physiologically acceptable salt thereof, in an amount from 50 to 400 mg per single dose.

8. The method of claim 1, wherein the nifuratel is administered in combination with, or in temporal proximity with at least one active principle selected from antibiotics, antifungal agents, antiseptic agents, pH modifiers, and probiotics.

9. The method of claim 8, wherein the antibiotic is selected from the group consisting of macrolide antibiotics, beta-lactam antibiotics, fluoroquinolones, aminoglycosides, and clindamycin.

10. The method of claim 8, wherein the antifungal agent is selected from the group consisting of 1-hydroxy-2-pyridone compounds and their salts, imidazole derivatives and their salts, polyene derivatives and their salts, allylamine derivatives and their salts, triazole derivatives and their salts, morpholine derivatives and their salts, griseofulvin and related compounds, undecylenic acid and its salts, tolnaphtate and its salts, and flucytosine and its salts.

11. The method of claim 8, wherein the antifungal agent is a plant extract selected from tea tree oil (*Melaleuca alternifolia*), lavender oil (*Lavandula officinalis* chaix) and the leaf extract of the neem tree (*Azadirachta indica*).

12. The method of claim 8, wherein the antiseptic agent is selected from benzalkonium-chlorid, benzethonium-chlorid, cetrimonium-bromid, chlorhexidin, dequaliniumchlorid, triclocarban, triclosan, salicylic acid, benzoic acid and salts thereof, and p-hydroxybenzoic acid and its esters.

13. The method of claim 8, wherein the pH modifier is selected from ascorbic acid, acetic acid, lactic acid, and salts thereof.

14. The method of claim 8, wherein the probiotic is selected from species of the genus *Lactobacillus*.

15. The method of claim 9, wherein the macrolide antibiotic is selected from the group consisting of erythromycin, oleandomycin, flurithromycin, azithromycin, claritromycin, and salts thereof.

16. The method of claim 9, wherein the beta-lactam antibiotic is selected from the group consisting of including penicillin, ampicillin, amoxicillin, and salts thereof.

17. The method of claim 9, wherein the fluoroquinolone is selected from the group consisting of ofloxacine, norfloxacine, ciprofloxacine, and salts thereof.

18. The method of claim 9, wherein the aminoglycoside is selected from the group consisting of gentamycin, amikacin, kanamycin, neomycin, and salts thereof.

19. The method of claim 10, wherein the 1-hydroxy-2-pyridone compound is selected from the group consisting of ciclopirox, rilopirox, piroctone, ciclopirox and olamine.

20. The method of claim 10, wherein the imidazole derivative is selected from the group consisting of clotrimazole, econazole, isoconazole, ketoconazole, miconazole, tioconazole, bifonazole, fenticonazole and oxiconazole.

21. The method of claim 10, wherein the polyene derivative is selected from the group consisting of nystatin, natamycin and amphotericin.

22. The method of claim 10, wherein the allylamine derivative is selected from the group consisting of naphtifine and terbinafine.

23. The method of claim 10, wherein the triazole derivative is selected from the group consisting of fluconazole, itraconazole, terconazole and voriconazole.

24. The method of claim 10, wherein the morpholine derivative is selected from the group consisting of amorolfine and morpholines.

25. The method of claim 10, wherein the undecylenic acid is selected from the group consisting of zinc and calcium salts of undecylenic acid.

* * * * *